United States Patent [19]

Labes

[11] 4,011,046
[45] Mar. 8, 1977

[54] LIQUID CRYSTAL QUANTITATIVE ANALYSIS METHOD FOR OPTICALLY ACTIVE COMPOUNDS

[75] Inventor: Mortimer M. Labes, Philadelphia, Pa.

[73] Assignee: Temple University, Philadelphia, Pa.

[22] Filed: Nov. 12, 1975

[21] Appl. No.: 631,100

[52] U.S. Cl. .......................................... 23/230 LC
[51] Int. Cl.² ............... G01N 21/46; G01N 23/201; G01N 23/207
[58] Field of Search ........ 23/230 R, 230 B, 230 LC

[56] References Cited
OTHER PUBLICATIONS

Van Meter, J. P., "Chemistry of Liquid Crystals," Eastman Organic Chemical Bulletin 45, No. 1, (1973).
Buckingham et al., Chem. Phys. Lett. 3, 540, (1969).
Haas, et al., ibid. 14, 95 (1972).
Hakemi et al., J. Chem. Phys. 61, No. 10, 4020, (1974).
Baessler, et al., Ibid. 52, No. 2, 631, (1970).
Gaubert, Comptes Rendues 207, 1052, (1938).
Gaubert, Ibid. 208, 43, (1939).
Penot, et al., Tetrahedron Letters 37, 4031, (1968).
Cano, et al., C. R. Acad. Sc. Paris t.259, 352, (1964).
Adams et al., "The Effective Rotary Power of the Fatty Esters of Cholesterol," *Liquid Crystals and Ordered Fluids*, (New York: Plenum Press, 1970), 463.

*Primary Examiner*—R.E. Serwin
*Attorney, Agent, or Firm*—Miller & Prestia

[57] ABSTRACT

Using a standardized cell containing a thin layer of an aligned nematic liquid crystalline material, a relationship is determined between concentration of an optically active solute material in the liquid crystal layer and line spacing in a pattern produced by differential light refraction, upon the injection of different amounts of the optically active compound. Subsequently, quantitative analysis of a sample containing the optically active compound is accomplished by injecting a known amount of the sample into a second identical standardized cell, observing the line spacing of refracted light in the second cell and comparing it to the relationship determined in the first cell. Optically active compounds analyzable in this manner include steroids and cholesteryl esters. A preferred nematic liquid crystalline material is n-p-methoxybenzylidene-p-n-butylaniline. A specific system described consists of cholesteryl-2-methyl valerate in homeotropically aligned n-p-methoxybenzylidene-p-n butylaniline with a layer thickness in the cell of 12.7 microns.

31 Claims, 2 Drawing Figures

Homeotropically aligned cholesteric phase consisting of 0.7% of cholesteryl-2-methylvalerate in MBBA. Magnification 150x. The pitch of this sample is ≃105μ.

Fig. 1. Homeotropically aligned cholesteric phase consisting of 0.7% of cholesteryl-2-methylvalerate in MBBA. Magnification 150x. The pitch of this sample is ≈105μ.

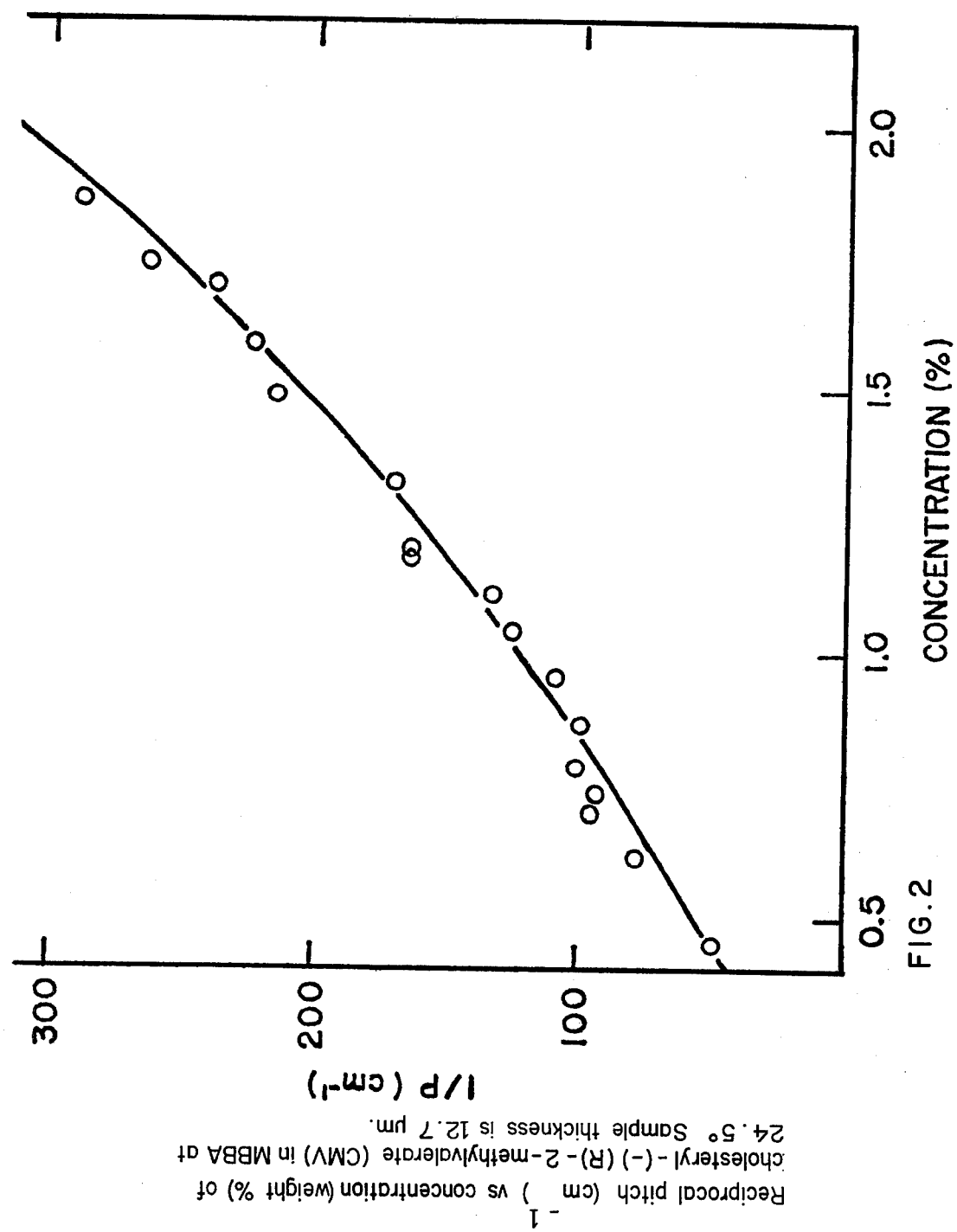
FIG.2 Reciprocal pitch (cm$^{-1}$) vs concentration (weight %) of cholesteryl-(-)-(R)-2-methylvalerate (CMV) in MBBA at 24.5°. Sample thickness is 12.7 μm.

LIQUID CRYSTAL QUANTITATIVE ANALYSIS METHOD FOR OPTICALLY ACTIVE COMPOUNDS

This invention pertains to a quantitative analytical method for an optically active compound. More specifically, it pertains to such method involving differential light refraction caused by injection of the optically active compound in a standardized cell containing a nematic liquid crystalline material.

There is a continuing need for improved methods, particularly methods which may be performed automatically, for quantitatively analyzing samples containing very small quantities of specific compounds. In many cases, the compounds to be analyzed are drugs or foreign substances found in the blood stream or urine. Typically, quantitive analysis for these compounds which are present in very low concentrations is difficult and the available methods are not readily adaptable to automatic control to produce better reproducibility It is therefore the general object of the present invention to provide an improved method for quantitively analyzing for optically active compounds in a highly dilute sample.

It is a more specific object of this invention to provide a quantitive analysis method for such optically active compound which is conductive to automatic control and a high degree of reproducibility.

These objects, and others which will be apparent in the course of the subsequent discussion, are met by a method in which a relationship or curve is first determined for the line spacing of differentially refracted light and concentration of an optically active compound in a nematic liquid crystalline material oriented in a standardized cell. In the cell, the nematic liquid crystalline material is sandwiched between transparent cell face members and the liquid crystals are aligned either parallel or perpendicular to the face members. Thereafter, a sample containing the optically active compound in low concentration is injected, in a controlled volume, into a second standardized cell identical with the first and the spacing of refracted light is observed and compared to the curve or relationship established in the first cell. On the basis of this comparison, the quantity of the optically active compound in the sample in the second cell is then as certainable.

Generally the liquid crystal layer will be from 6 to 150 microns in thickness and the side dimensions of the aligned area of the cell will be from 0.2 to 3 centimeters.

This invention may be better understood by reference to the following detailed description, taken in conjunction with the subjoined claims and the drawings, in which:

FIG. 1 is a photomicrograph of the pattern produced by differential refraction of light in a homeotropically aligned nematic liquid crystalline cell into which an optically active compond has ben injected; and FIG. 2 is a graph showing the relationship between line spacing (more specifically, the reciprocal of the pitch of the helical distortion of the liquid crystal, upon which line spacing is dependent), in a pattern such as that shown in FIG. 1, and concentration of the optically active compound in the standardized cell.

Referring more specifically to FIG. 1, there is shown the texture pattern, at a magnification of 150x, produced in a standardized cell used in the method of the present invention. The nematic layer in this cell consists of n-p-methoxybenzylidine-p-n-butylaniline (MBBA), in a thickness of 12.7 microns, homeotropically aligned (optic or molecular axis perpendicular to the transparent cell face members; axis of helical distortion of liquid crystals, induced by solute, parallel to cell face members). The optically active solute compound was chloesteryl-2-methylvalerate in a concentration of 0.7%.

In FIG. 2, it is seen that the reciprocal pitch of the helical distortion of the liquid crystals produced by injection of the cholesteryl-2-methylvalerate in MBBA is directly proportional to the concentration of that optically active compound in MBBA as determined in a standardized cell. The relationship deviates from linearity as the concentration becomes higher but calibration allows one to determine concentration from the observed pitch throughout a predetermined range.

It should be understood that the pitch of a helix induced in the axes of the nematic liquid crystals in the cell (the pitch actually being the distance along the length of the helix required for the helical distortion to describe a 360° rotation) produces a pattern in which the repeating bright or thick lines represent regions where the liquid crystal helical distortion is turned 180°; therefore the distance between these repeating helical distortion bright lines is the half-pitch of the helix. "Line spacing" is therefore directly related to pitch and, as a matter of convenience, a relationship such as that shown in FIG. 2 may be determined as a function of either pitch or the reciprocal of pitch or "line spacing".

Note also that while this invention has been described with reference to a "first cell" and a "second cell", the determination of the concentration relationship and indeed the analysis itself may be accomplished in a single cell, in which the nematic liquid crystalline phase is replaced for the various tests involved in the standardization or determination of the relationship and in the quantitative analysis itself.

In the specific example shown and described with reference to the figures, the nematic liquid crystalline material is "homeotropically aligned". With such a crystalline alignment, the axes of the crystals are perpendicular to the cell walls and the "director" of the helix formed by the crystalline axis precesses with increasing distance from the cell wall. A helicoidal array is thus established with the helix axis perpendicular to the wall. Similar results may be achieved with alignment of the liquid crystal axes parallel to the cell wall, in alignment referred to as "homogeneous".

Alignment of the liquid crystalline phase in the standardized cell used in the quantitative analysis method of this invention can be accomplished in a variety of ways, including mechanically surface scribing the interior surfaces of the cell wall, or deposition of organic or inorganic thin films, including silane coupling agents and silicon oxide coatings, which induce molecular alignment. The thickness of the nematic liquid crystal layer is limited by the fact the alignment is more difficult to produce as thickness increases. Because pitch is inversely proportional to concentration of the optically active compound injected into the nematic liquid crystalline layer, line spacing in the diffraction pattern is generally observable only a very low concentrations of the optically active compound.

In general, any optically active compound may be the subject of the quantitative analysis method of this invention. In particular, cholesteryl esters and steroids are optically active compounds known to be analyzable in accordance with the present invention. The choloesteryl-2-methylvalerate is but one example of such a cholesteryl ester. Other compounds within this group include: cholesterol, cholesteryl halides, cholesteryl straight chain fatty acid esters, such as cholesteryl nonanoate, stearate, etc.; cholesteryl carbonate esters, cholesteryl benzoates, and cholesteryl s-alkyl thiocarbonates. Also other steroidal compounds, such as stigmasterol and its derivatives, cholestadienols and cycloartanyl esters are known to behave in the same manner. Still other optically active compounds analyzable in accordance with the present invention include optically active organic bases, such as optically active amphetamines or derivatives thereof such as dextroamphetamine; optically active alkaloids, such as a morphine alkaloid, an indole alkaloid, a cinchona alkaloid, an ergot alkaloid, examples of which include morphine and codeine; an optically active terpenoid alcohol; an optically active sugar compound or sugar derivative; or a chiral nematic liquid crystal.

The present inventive method is thought to be applicable to standardized cells using any of a variety of nematic liquid crystalline materils, including nematogenic Schiff bases, such as MBBA used in the example set forth above. Other nematic liquid crystals which may be used include substituted azoxybenzene nematogens, such as "Phase V," (a composition comprising p-methoxy-p-'-n-butyl azoxybenzene, commericially available from E. Merck & Co., Darmstadt, West Germany), substituted phenyl-4-benzoyl oxybenzoate, substituted benzoyloxy benzoate, substituted biphenyls, such as p-n-hetyl-p'-cyanobiphenyl and other nematic mixtures of these nematogenic materials, such as mixtures of one or more Schiff bases, including for example a mixture of MBBA (above) and ethoxybenzylidene-butyl aniline (EBBA). In addition, compensated mixtures of cholesteric liquid crystals may also be used as the nematic liquid crystalline phase. An example of such a mixture is that consisting of:

1.75 parts by weight of cholesteryl chloride, (CC) and
1.00 parts by weight of cholesteryl myristate, (CM) compensated at 43° C.

While this invention has been described with reference to specific processes, compositions and conditions, it should be understood that the invention is not limited thereto. The appended claims therefore are intended to be construed to cover all methods within the true spirit and scope of the present invention.

I claim:

1. Method for quantitatively analyzing a sample, for a specific optically active compound contained therein, by first determining the relationship between line spacing of differentially refracted light and concentration of said optically active compound in a nematic liquid crystalline material oriented in a first standardized cell consisting of a thin layer of said liquid crystalline material disposed between transparent cell face members, and subsequently injecting a preselected amount of said sample into the nematic liquid crystalline layer of a second standardized cell identical with said first cell, observing the line spacing of refracted light in said second cell and comparing it to the relationship determined in said first cell and, on the basis of said comparison, determining the quantity of said optically active compound in said second cell.

2. Method, as recited in claim 1, wherein the thickness of said nematic liquid crystalline layer is from 6 to 150 microns and the side dimensions of the aligned liquid crystalline layer area is from 0.2 to 3 centimeters.

3. Method, as recited in claim 1, wherein said nematic liquid crystalline material is a nematogenic Schiff base, such as n-p-methoxybenzylidene-p-n-butyl aniline.

4. Method, as recited in claim 1, wherein said nematic liquid crystalline material is a compensated mixture of cholesteric liquid crystals.

5. Method, as recited in claim 1, wherein said nematic liquid crystalline material is a mixture of cholesteryl chloride and cholesteryl myristate, compensated at 43° C.

6. Method, as recited in claim 1, wherein said nematic liquid crystalline material is a substituted azoxybenzene nematogen.

7. Method, as recited in claim 1, wherein said nematic liquid crystalline material is p-methoxy-p'-n-butyl azoxybenzene.

8. Method, as recited in claim 1, wherein said nematic liquid crystalline material is substituted phenyl-4-benzoyl oxy benzoate.

9. Method, as recited in claim 1, wherein said nematic liquid crystalline material is substituted benzoyloxy benzoate.

10. Method, as recited in claim 1, wherein said nematic liquid crystalline material is a substituted biphenyl.

11. Method, as recited in claim 1, wherein said nematic liquid crystalline material is p-n-heptyl-p' cyanobiphenyl.

12. Method, as recited in claim 1, wherein said liquid crystalline material is a mixture of one or more nematogenic materials.

13. Method, as recited in claim 1, wherein said nematic liquid crystalline material is homeotropically aligned.

14. Method, as recited in claim 1, wherein said nematic liquid crystalline material is homogeneously aligned.

15. Method, as recited in claim 1, wherein said optically active compound is a steroidal compound.

16. Method, as recited in claim 1, wherein said optically active compound is a cholesteryl derivative.

17. Method, as recited in claim 1, wherein said optically active compound is cholesteryl-2-methyl valerate.

18. Method, as recited in claim 1, wherein said optically active compound is an optically active amphetamine.

19. Method, as recited in claim 1, wherein said optically active compound is optically active dextroamphetamine.

20. Method, as recited in claim 1, wherein said optically active compound is an optically active organic acid.

21. Method, as recited in claim 1, wherein said optically active compound is optically active tartaric acid.

22. Method, as recited in claim 1, wherein said optically active compound is an alkaloid compound.

23. Method, as recited in claim 1, wherein said optically active compound is a morphine alkaloid.

24. Method, as recited in claim 1, wherein said optically active compound is an indole alkaloid.

25. Method, as recited in claim 1, wherein said optically active compound is a cinchona alkaloid.

26. Method, as recited in claim 1, wherein said optically active compound is an ergot alkaloid.

27. Method, as recited in claim 1, wherein said optically active compound is morphine.

28. Method, as recited in claim 1, wherein said optically active compound is codeine.

29. Method, as recited in claim 1, wherein said optically active compound is an optically active terpenoid alcohol.

30. Method, as recited in claim 1, wherein said optically active compounds is a chiral nematic liquid crystal.

31. Method, as recited in claim 1, wherein said optically active compound is an optically active sugar compound or sugar derivative.

* * * * *